(12) United States Patent
Tittelbach et al.

(10) Patent No.: US 9,833,547 B2
(45) Date of Patent: Dec. 5, 2017

(54) DRUG-COATED BALLOON CATHETER AND METHOD FOR THE PRODUCTION THEREOF

(71) Applicant: Biotronik VI Patent AG, Baar (CH)

(72) Inventors: Michael Tittelbach, Nuremberg (DE); Raimund Moehl, Forch (CH); Alwin Schwitzer, Buelach (CH); Matthias Wesselmann, Glattfelden (CH); Bodo Quint, Oberglatt (CH); Patrice Bachmann, Winterthur (CH)

(73) Assignee: Biotronik VI Patent AG, Baar (CH)

( * ) Notice: Subject to any disclaimer, the term of this patent is extended or adjusted under 35 U.S.C. 154(b) by 1 day.

(21) Appl. No.: 15/008,873

(22) Filed: Jan. 28, 2016

(65) Prior Publication Data

US 2016/0144077 A1  May 26, 2016

Related U.S. Application Data

(62) Division of application No. 12/767,462, filed on Apr. 26, 2010, now abandoned.

(30) Foreign Application Priority Data

May 7, 2009 (DE) .......................... 10 2009 002 893

(51) Int. Cl.
  *A61L 29/16* (2006.01)
  *A61L 29/08* (2006.01)

(52) U.S. Cl.
  CPC ............ *A61L 29/16* (2013.01); *A61L 29/085* (2013.01); *A61L 2300/606* (2013.01); *A61L 2420/02* (2013.01); *A61L 2420/06* (2013.01)

(58) Field of Classification Search
  CPC ................................. A61M 29/02; A61F 2/02
  USPC .......................................... 424/423; 606/194
  See application file for complete search history.

(56) References Cited

U.S. PATENT DOCUMENTS

| | | | |
|---|---|---|---|
| 5,100,429 A | 3/1992 | Sinofsky et al. | |
| 5,290,306 A * | 3/1994 | Trotta | A61M 25/10 604/103.01 |
| 5,304,121 A | 4/1994 | Sahatjian | |
| 6,093,463 A | 7/2000 | Thakrar | |
| 7,419,696 B2 | 9/2008 | Berg et al. | |
| 7,658,966 B2 | 2/2010 | Kokish | |
| 2004/0086542 A1 | 5/2004 | Hossainy et al. | |
| 2005/0226991 A1 | 10/2005 | Hossainy et al. | |

(Continued)

FOREIGN PATENT DOCUMENTS

| | | |
|---|---|---|
| EP | 0357369 A2 | 3/1990 |
| WO | 199505866 A1 | 3/1995 |

OTHER PUBLICATIONS

EP10156621.4 European Search Report dated Sep. 15, 2014.

(Continued)

*Primary Examiner* — Dah-Wei D Yuan
*Assistant Examiner* — Andrew Bowman
(74) *Attorney, Agent, or Firm* — Wagenknecht IP Law Group PC

(57) ABSTRACT

The invention relates to a drug-coated balloon catheter and to a method for producing the same. The balloon of the catheter includes (i) a main membrane, and (ii) an asymmetrical polymer membrane which is applied to an outside of the main membrane and into which at least one pharmaceutical active ingredient is introduced.

3 Claims, 1 Drawing Sheet

(56) References Cited

U.S. PATENT DOCUMENTS

| | | |
|---|---|---|
| 2006/0184112 A1 | 8/2006 | Horn et al. |
| 2006/0280858 A1 | 12/2006 | Kokish |
| 2007/0202147 A1* | 8/2007 | Kleiner .................. A61L 31/10 |
| | | 424/423 |
| 2007/0280988 A1 | 12/2007 | Ludwig et al. |
| 2010/0189876 A1 | 7/2010 | Kokish et al. |
| 2010/0198150 A1 | 8/2010 | Michal et al. |
| 2011/0092900 A1 | 4/2011 | Rubben |
| 2012/0003379 A1 | 1/2012 | Wang et al. |

OTHER PUBLICATIONS

Nunes and Peinemann. Eds. "Membrane Preparation." Membrane Technology in the Chemical Industry, pp. 6-11, Jan. 2001, Wiley-VCH Verlag GmbH, Germany.

* cited by examiner

DRUG-COATED BALLOON CATHETER AND METHOD FOR THE PRODUCTION THEREOF

CROSS REFERENCE TO RELATED APPLICATIONS

This is a divisional of U.S. patent application Ser. No. 12/767,462 filed Apr. 26, 2010, which claims benefit of priority to Germany patent application serial number DE 10 2009 002 893.5, filed on May 7, 2009; the contents of which is herein incorporated by reference in its entirety.

FIELD OF THE INVENTION

The invention relates to a drug-coated balloon catheter and to a method for producing the same.

BACKGROUND OF THE INVENTION

The use of balloon catheters is a preferred therapeutic method for a wide variety of indications in many areas of medical technology. In angioplasty and cardiology, for example, a dilation of constricted blood vessels by way of balloon dilation is proposed, releasing restenosis-inhibiting drugs at the same time. According to one variant, for this purpose the drugs are applied directly onto the balloon to be dilated. However, it has been found that in practice up to 80% of the adhering drug is not applied at the desired location of the vessel, but instead is dissolved beforehand by the body fluid present in the lumen and carried away. This increases the risk of undesirable systemic side effects of the drugs.

As a counter measure, it has been proposed, for example, to conduct the expansion of the balloon catheter over a dumbbell-shaped intermediate stage, in which the two ends of the balloon catheter shield the intermediate region coated with drugs from the lumen of the vessel. Thereafter, the balloon is fully expanded. Such a dumbbell-shaped balloon catheter used as an intermediate stage, however, is very complex to produce and handle and therefore prone to failure. In addition, it is impossible to prevent the drug from being rinsed out when irregular vessel geometries came into play.

A different approach would be to apply a coating receiving or covering the drug. The production of such a coating, however, is complex and catheters coated in this manner generally cannot be stored for a long time. The coating material must be biocompatible, and the properties of the drug and the coating system must be matched to each other in each individual case. In practice, this makes the implementation of such a drug-coated balloon catheter very complex, and it still does not provide the desired extent of safety for the local administration of the drug.

SUMMARY OF THE INVENTION

It is therefore the object of the invention to provide a drug-coated catheter, which solves or at least mitigates one or more the problems addressed above.

A first aspect of the present invention is a drug-coated balloon catheter having a balloon, comprising (i) a main membrane, and (ii) an asymmetrical polymer membrane which is applied to an outside of the main membrane and into which at least one pharmaceutical active ingredient is embedded.

Another aspect of the present invention is a method for producing a drug-coated balloon catheter, comprising the following steps: (a) providing a balloon blank having a main membrane; (b) wetting the main membrane with a homogeneous polymer solution comprising a solvent and a polymer; (c) inducing a phase separation of the polymer from the polymer solution by a measure selected from the group consisting of: (i) Temperature change, (ii) immersing the wetted balloon blank in a bath of a liquid which can be mixed with the solvent of the polymer solution, but which does not dissolve, or hardly dissolves, the polymer, and (iii) exposing the wetted balloon blank to an atmosphere which comprises a gaseous constituent which can be mixed with the solvent of the polymer solution, but does not dissolve, or hardly dissolves, the polymer.

DESCRIPTION OF THE DRAWINGS

The invention is described based on the attached drawings.

DETAILED DESCRIPTION OF THE INVENTION

Figure 1:
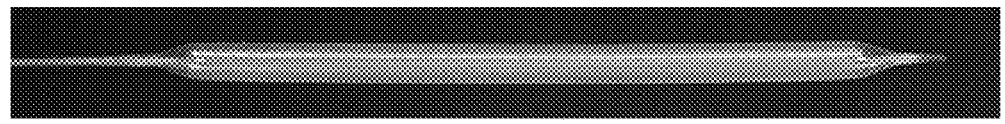
FIG. 1 shows an illustration of the balloon membrane of a balloon catheter modified using the method according to the invention.

A first aspect of the invention is to provide a drug-coated balloon catheter, the balloon of which includes: (i) a main membrane, and (ii) an asymmetrical polymer membrane which is present on an outside of the main membrane and into which at least one pharmaceutical active ingredient is introduced.

The balloon catheter according to the invention therefore includes a microporous asymmetrical polymer membrane on the outside of the balloon wall. This polymer membrane has a plurality of pores and micro-furrows, into which the drug to be applied is embedded in solute form or pure form. With respect to morphology, asymmetrical polymer membranes are characterized as having a higher density at the outsides thereof than at the bases thereof, which is to say on the side facing the main membrane. Accessibility of the cavities of the polymer membrane in the non-expanded state of the balloon is so low that any rinsing out of the drug by body fluid is significantly reduced or even prevented. It is only in the expanded state that the pores and micro-furrows at the top of the polymer membrane are dilated such that the incorporated active ingredient can be released without difficulty.

Accordingly, asymmetrical polymer membranes have a thin cover layer with suitable mechanical stability, which protects a porous structured located underneath. The term "asymmetrical membrane" summarizes this very morphology in one term and is also used in the literature (see, for example, Membrane Technology in the Chemical Industry, 2001 Wiley-VCH Verlag GmbH, Chapter 3, pages 6-11). The structure of asymmetrical polymer membranes is dependent on the production method thereof. Consequently, another aspect of the invention is directed at the production of such a drug-coated balloon catheter. The method includes the following steps: (a) providing a balloon blank having a main membrane; (b) wetting the main membrane with a homogeneous polymer solution including a solvent and a polymer; (c) inducing a phase separation of the polymer from the polymer solution by one of the following measures:

(i) Temperature change, (ii) immersing the wetted balloon blank in a bath of a liquid which can be mixed with the solvent of the polymer solution, but which does not dissolve, or hardly dissolves, the polymer (wet process), or (iii) exposing the wetted balloon blank to an atmosphere which includes a gaseous constituent which can be mixed with the solvent of the polymer solution, but does not dissolve, or hardly dissolves, the polymer (dry method).

After step (a), the method is therefore based on a balloon catheter having a balloon, the outer membrane wall is to be coated. For the purpose of the invention, it is immaterial whether this is a monolumen, multilumen, or multi-layer catheter. In any case, the outside of the balloon, hereinafter referred to as the main membrane, is modified by deposition of the asymmetrical polymer membrane.

The main membrane, at least on the outside thereof, preferably includes a polymer material that is commonly used for these purposes, in particular the polymer material of the main membrane is selected from the group including of polyurethane, polyether-polyurethane, polyethylene terephthalate, polybutylene terephthalate, polyamide, and also copolymers and blends thereof. Polyamides are particularly preferred because they have particularly high strength.

Typical balloon materials are usually semicrystalline thermoplastic resins, wherein in the PTCA/PTA field primarily polyamides, polyethylene terephthalate (PET), or polybutylene terephthalate (PBT), and the copolymers and blends thereof are used. Polyurethanes are gaining increasing importance as alternative materials for expandable and adaptable balloon applications. Typical occlusion balloons are frequently made of latex.

Furthermore, a homogeneous polymer solution is provided, including a solvent having a polymer that is suited for developing the asymmetrical polymer membrane. Polyurethanes or polyether-polyurethanes are polymers that are particularly preferred. However, it is also possible to use other polymers which can be homogeneously dissolved in a solvent, such as aromatic polyimides, polyethersulfones, polypropylene, cellulose, and cellulose derivatives.

The solvent should be selected such that a sufficiently high concentration of the polymer for the method is possible. In addition, the properties of the solvent significantly influence the phase inversion. Suitable solvents include in particular dimethylformamide (DMF) and tetrahydrofurane (THF). The latter is particularly preferred, because it is easy to remove from the product as a result of the relatively low boiling point thereof and the excellent water solubility thereof. In the solvents mentioned above, in particular polyurethane and polyether-polyurethane have particularly high solubility.

The homogeneous polymer solution is applied in step (b) onto the region of the balloon catheter to be coated, be it by immersion into the solution or by spraying on the same, for example. Wetting can take place in particular in the expanded state of the balloon blank, so that the regions of the polymer membrane close to the surface are further compacted upon deflation, making accessibility to the inner structure from the outside more difficult.

The process of phase inversion of the initially homogeneous polymer solution is initiated by a temperature change (alternative (i) step (c)), by immersing the wetted balloon blank into a bath of a fluid that can be mixed with the solvent of the polymer solution, but which does not dissolve, or hardly dissolves, the polymer (wet process; alternative (ii) step (c)), or by exposing the wetted balloon blank to an atmosphere which includes a gaseous constituent which can be mixed with the solvent, but which does not dissolve, or hardly dissolves, the polymer (dry method; alternative (iii) step c)).

During the thermal process, typically a low-molecular compound acts as the solvent at high temperatures, but dissolves the powder only insufficiently at lower temperatures. Such a process lends itself whenever the polymer to be deposited has poor solution properties, such as polypropylene.

Isothermal phase separation, in particular after the drying process, is preferred in the present case. In this process, the polymer solution is exposed to a liquid or gaseous constituent, which gradually spreads in the polymer solution, starting from the outside of the liquid polymer film. However, this constituent cannot dissolve, or hardly dissolves, the polymer, so that the polymer is precipitated by way of phase separation. Such a system is particularly easy to implement, for example, when using a THF polymer solution: here, water or a water/alcohol mixture can be used as the non-solvent for the polymer.

The morphology of the asymmetrical polymer membrane forming over the course of the method can be influenced by the selected method parameters. The underlying mechanisms of the process are complex and have so far not been conclusively clarified. For practical applications, however, parameters are known, which result in structures of a predominantly foam-like, microporous nature or having finger-like cavities/micro-furrows. The foam-like structure is preferably formed when the polymer concentration in the polymer solution rises, the viscosity of the polymer solution is increased, such as by adding a cross-linking agent, or mixtures of solvents and non-solvents are used. For the present purposes, a structure representing a mixture of both structure types is preferred.

In the simplest case, the pharmaceutical active ingredient can already be present in the polymer solution. This drastically simplifies the manufacturing process. However, it is also conceivable to apply a solution of a pharmaceutical active ingredient, or the pure active ingredient, onto the dried and purified polymer membrane after the asymmetrical polymer membrane has been produced. This application should be carried out in particular in the expanded state of the balloon in order to facilitate embedding of the material into the inner lumen of the polymer layer. Ideally, the active ingredient, or the active ingredient solution, has minimal interaction with the polymer membrane in order to facilitate the release of the agent. This can be achieved, for example, by adding suitable additives to the polymer solution.

The invention will be explained in more detail hereinafter based on one exemplary embodiment.

Example: Production of a Coated Balloon Catheter

A balloon catheter having a balloon membrane comprising polyamide was closed distally with a silicone tube, inflated at low pressure (3-5 bar), and immersed in a solution. The catheter was pulled out of the immersion solution in a continuous and slow movement, wherein it should be noted that the speed of pulling it out and the viscosity of the polymer solution influence the applied layer thickness of the polymer membrane to be produced.

The coagulation of the polymer from the polymer solution is done by introducing the balloon catheter coated with the polymer solution into a conditioning chamber having an atmosphere of isopropanol/water (produced by heating a 50/50 isopropanol/water mixture at 70° C.).

Figure 2:
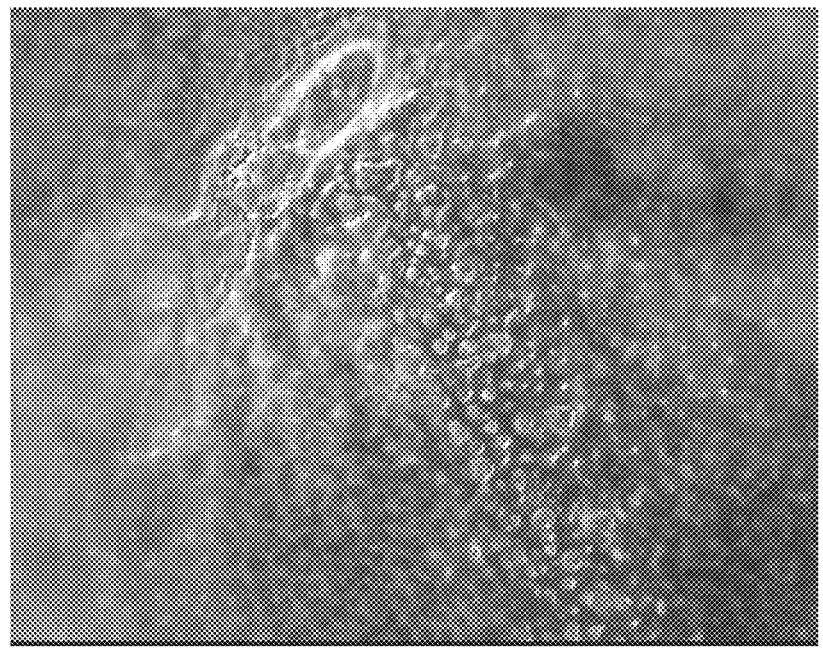
FIG. 2 shows an enlarged section of the surface of the balloon membrane of FIG. 1.

After 10 minutes, the balloon was removed from the conditioning chamber, rinsed several times with distilled water, and dried. FIGS. 1 and 2 illustrate the morphological changes on the surface of the balloon catheter.

The conical region of the balloon, which is of interest for the coating, is defined proximally by the depth of immersion into the polymer solution and by the distal subsequent removal of the polymer coating by way of a solvent.

In the inflated state, the balloon catheter can then be wetted with an active ingredient solution, which is embedded into the cavities of the polymer membrane that were produced.

What is claimed is:

1. A method for producing a drug-coated balloon catheter, comprising the following steps:
    a) providing a balloon blank having a main membrane;
    b) wetting the main membrane with a homogeneous polymer solution comprising a solvent and a polymer;
    c) inducing a phase separation of the polymer from the polymer solution by a measure selected from the group consisting of:
        (i) temperature change,
        (ii) immersing the wetted balloon blank in a bath of a liquid which can be mixed with the solvent of the polymer solution, but which does not dissolve, or hardly dissolves, the polymer, and
        (iii) exposing the wetted balloon blank to an atmosphere which comprises a gaseous constituent which can be mixed with the solvent of the polymer solution, but does not dissolve, or hardly dissolves, the polymer;
    d) drying the balloon after the phase separation, and subsequently embedding a pharmaceutical active ingredient in the polymer membrane by applying an active ingredient solution, or a pure active ingredient, onto the polymer membrane in the expanded state of the balloon blank, wherein the pharmaceutical active ingredient or the pure active ingredient is embedded into the inner lumen of the polymer membrane.

2. The method according to claim 1, wherein the polymer solution is a solution of polyurethane or polyether-polyurethane in tetrahydrofurane (THF) or dimethylformamide (DMF).

3. The method according to claim 1, wherein step c) is carried out in an expanded state of the balloon blank.

* * * * *